Figure 1:
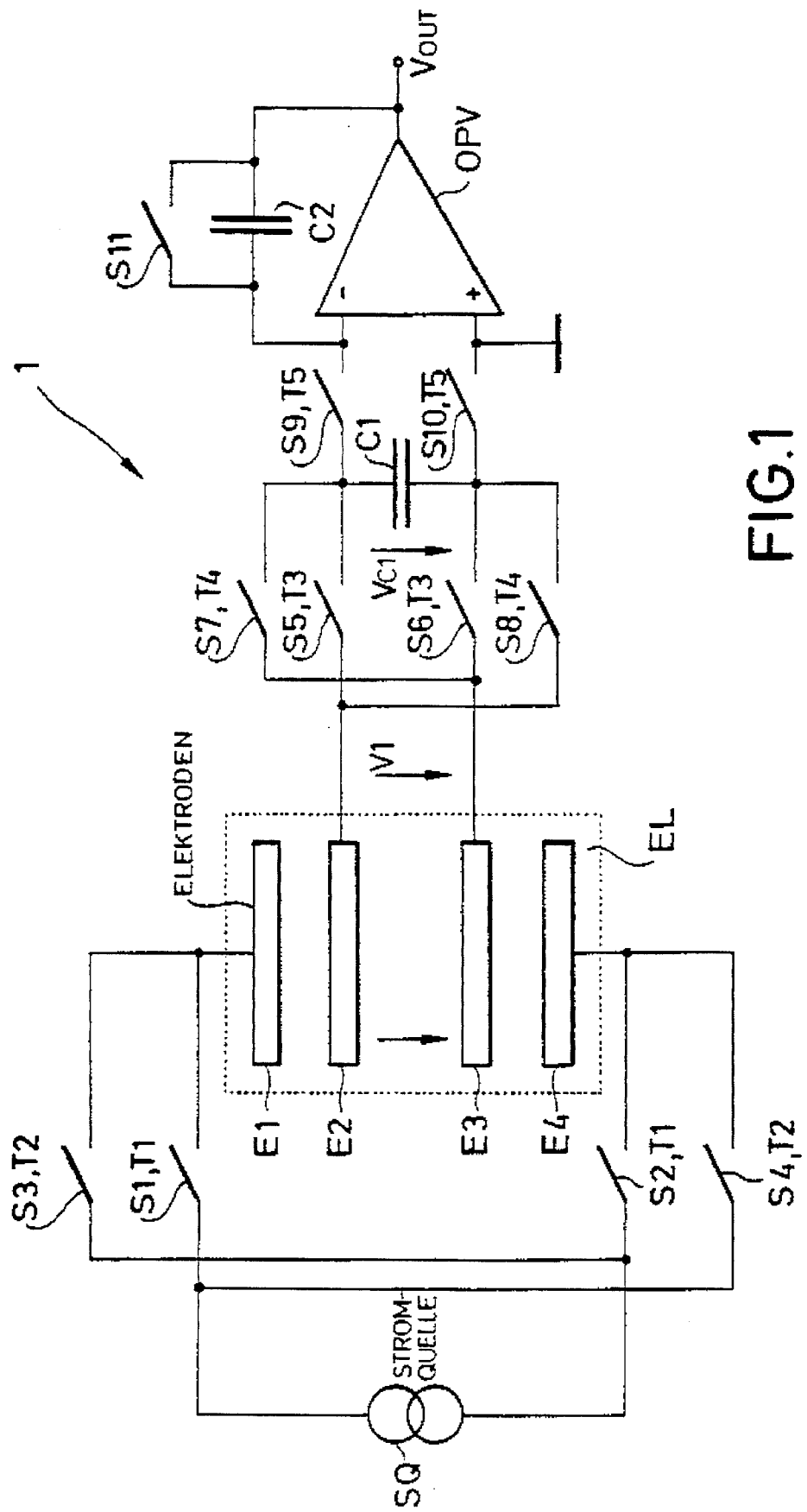

United States Patent [19]

Kordas

[11] Patent Number: 5,543,717
[45] Date of Patent: Aug. 6, 1996

[54] INTEGRABLE CONDUCTIVITY MEASURING DEVICE

[75] Inventor: Norbert Kordas, Essen, Germany

[73] Assignee: Fraunhofer-Gesellschaft zur Forderung der Angewandten Forshung e.v., Munich, Germany

[21] Appl. No.: 119,243

[22] PCT Filed: Mar. 23, 1992

[86] PCT No.: PCT/DE92/00242

§ 371 Date: Sep. 21, 1993

§ 102(e) Date: Sep. 21, 1993

[87] PCT Pub. No.: WO92/18856

PCT Pub. Date: Oct. 29, 1992

[30] Foreign Application Priority Data

Apr. 20, 1991 [DE] Germany .................. 41 13 033.2

[51] Int. Cl.⁶ .................................................. G01N 27/06
[52] U.S. Cl. .................. 324/444; 324/439; 324/446; 324/715
[58] Field of Search ................ 330/9, 7, 51, 10; 307/110, 353; 324/439, 444, 446, 715

[56] References Cited

U.S. PATENT DOCUMENTS 3,495,164  2/1970  Dauphinee .
3,757,205  9/1973  Dauphinee .
4,656,427  4/1987  Dauphinee .
4,833,413  5/1989  Head .
4,988,952  1/1991  Seuastopoulus .......................... 330/51
5,142,238  8/1992  White ...................................... 330/51

FOREIGN PATENT DOCUMENTS 0094811  7/1981  Japan .......................................... 330/9

*Primary Examiner*—Kenneth A. Wieder
*Assistant Examiner*—Jose M. Solis
*Attorney, Agent, or Firm*—Wolf, Greenfield & Sacks, P.C.

[57] ABSTRACT

A conductivity measuring device for measuring the electric conductivity of liquids has a current source device with current electrodes connectable thereto, via which a current can be fed into the liquid, and a measuring circuit connected to two voltage electrodes.

In order to reduce measuring errors on account of polarization effects, the current source device in accordance with the invention, generates the current having the rectangular waveform, wherein the measuring circuit is implemented as switched capacitor circuit comprising a measuring capacitor being connectable to and disconnectable from the voltage electrodes via a switch arrangement in time dependency of the path of the current having the rectangular waveform.

9 Claims, 2 Drawing Sheets

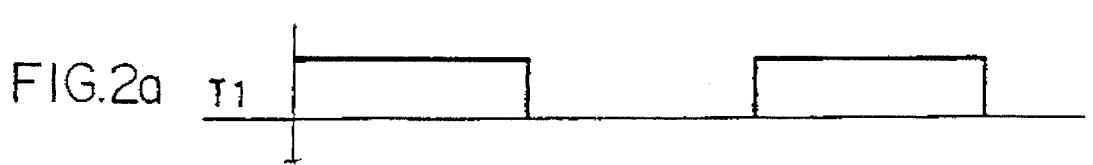
FIG.2a T1
FIG.2b T2
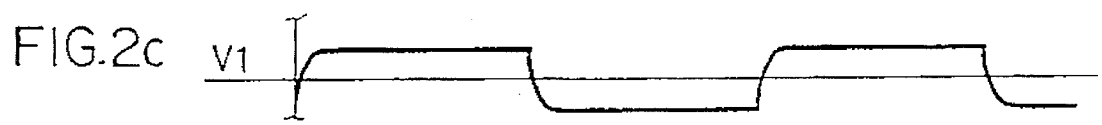
FIG.2c V1
FIG.2d T3
FIG.2e T4
FIG.2f T5
FIG.2g $V_{C1}$
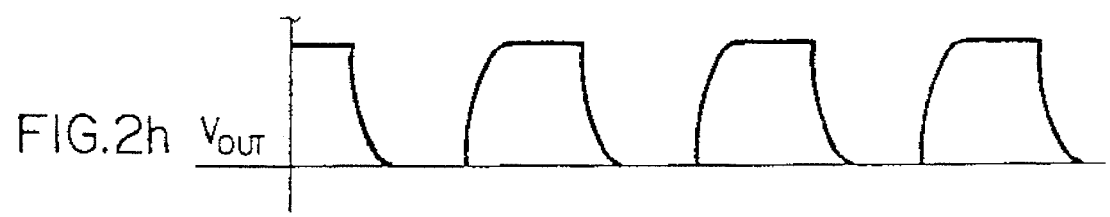
FIG.2h $V_{OUT}$

INTEGRABLE CONDUCTIVITY MEASURING DEVICE

The present invention relates to an integrable conductivity measuring device for measuring the electric conductivity of liquids with a current source device which is connected to two current electrodes, over which a current with a rectangular waveform can be fed to the liquid, and with a measuring circuit is connected to two voltage electrodes for determining the voltage drop between the two voltage electrodes, which is dependent on the electric conductivity of the investigated liquid.

For determining the electric conductivity of a liquid, it is general knowledge to impress a current into a liquid and to measure the voltage drop therein which is inversely proportional to the conductivity of the liquid.

In the simplest version only two electrodes are used. The current is impressed in the liquid via these two electrodes and simultaneously the voltage drop is measured by these two electrodes. On this occasion so-called polarization effects occur which distort the actual measuring signal. These effects always occur when current flows over a boundary layer between an electrode and an electrolyte. Since a flow of current in an electrolyte is connected with ion migration, ions of one charge-type accumulate at the boundary layer between the electrolyte and the electrode weakening the original field and reducing the measuring signal.

In order to eliminate this disadvantage, conductivity measuring devices with a so-called four-electrode-arrangement are used, wherein a current source with two current electrodes is provided for impressing the measuring current. Two further electrodes, which can be considered as voltage electrodes, serve for measuring the voltage drop via the liquid. The voltage drop measured by the voltage electrodes is amplified by a downstream high-resistance amplifier. On account of the high input impedance of the amplifiers, the current flowing via the voltage electrodes can be kept small, so that in this measuring method the polarization effects can be reduced, on account whereof an improved measuring accuracy is achieved as compared to the conductivity measurement by way of only two electrodes. However, also in the four-electrode-arrangement the measuring current flowing via the voltage electrodes leads to a polarization and consequently to a distortion of the measuring signal.

From U.S. Pat. No. 4,656,427 a conductivity measuring device of the afore-mentioned kind is already known, working with a four-electrode-arrangement. Two current electrodes can be charged with a current having a rectangular waveform. Two voltage electrodes provided with downstream capacitors for separating dc potentials serve to detect the dynamic change in potential on account of the rectangular alternating current impressed in the liquid to be measured. This signal is amplified by a subsequent evaluation circuit, provided with an additional capacitor connected in series, for separating offset-currents, and is displayed after analog-to-digital conversion on a display unit.

It is furthermore known in conductivity measuring devices of the afore-described type to produce the impressed current as sinusoidal alternating current in order to prevent decomposition processes in the liquid by this measure, which would occur in the case of a measurement with impressed direct current.

Proceeding from the above-mentioned prior art the present invention is based on the object of further developing a conductivity measuring device of the afore-mentioned kind so that an improved measuring accuracy is obtained.

According to the invention this object is achieved by an integrable conductivity measuring device for measuring the electric conductivity of liquids, comprising a current source device connectable to two current electrodes via which a current with a rectangular waveform can be fed into the liquid, and a measuring circuit connected to two voltage electrodes for determining the voltage drop between the voltage electrodes which is dependent on the electric conductivity of the investigated liquid, wherein the measuring circuit is a switched capacitor circuit having a measuring capacitor, an amplifying circuit with a feedback capacitor arranged in the feedback branch thereof, and a switch means by means of which the measuring capacitor is connected in time-dependency on the behaviour of the current having the rectangular waveform in one switching condition with the voltage electrodes and in another switching condition with the inputs of the amplifying circuit.

The invention is based on the finding that by using a current source device which produces a current having a rectangular waveform in combination with a switched capacitor circuit type measuring circuit, measuring errors due to polarization effects can be completely avoided.

The conductivity measuring device according to the invention can be implemented as integrated circuit so that it can be implemented including the electrodes on one single substrate. This allows for the conductivity measuring device according to the invention to be employed for measurement within very small sample volumes or for measurement at places inaccessible to conductivity measuring devices according to prior art, as for example in the field of invasive medical diagnostics.

Due to the integrability of the conductivity measuring device according to the invention it is less susceptible to irradiated disturbances than conductivity measuring devices according to the prior art, in which always longer cable connections are used between the electrodes and the evaluation electronic system. Thus the conductivity measuring device according to the invention also qualifies for use in ambience conditions with strong electromagnetic noise fields.

The integrable conductivity measuring device according to the invention will be explained in the following in closer detail and with reference to the enclosed drawings.

FIG. 1 is a wiring diagram of the conductivity measuring device according to the invention; and FIGS. 2a–2h are a set of time-dependency diagrams of currents and voltages as they occur in the conductivity measuring device according to FIG. 1, all having the same time axis.

The preferred embodiment of the integrable conductivity measuring device of the invention as shown in FIG. 1, which will be designated in its entirety hereinafter by the reference number 1, includes a current source SQ for producing an impressed direct current, which is connectable via first to fourth switches S1, S2, S3, S4 in dependence of their switching condition in a first polarity or in a polarity opposite to the first polarity, to two current electrodes E1, E4.

The current electrodes produce a current having the rectangular waveform without any dc-portion in an electrolyte EL.

A control device (not shown) controls the first to fourth switches S1 to S4 such that the current source SQ is connected alternately during a first period of time T1 in the first polarity and in a second period of time T2 in a second polarity with the current electrodes E1, E4. The first and the second periods of time T1, T2 have the same length.

Two voltage electrodes E2,E3 are arranged between the current electrodes E1, E4 in the electrolyte EL, measuring the voltage drop V1 over the electrolytes occurring between the current electrodes E1, E4 due to the impressed current having the rectangular waveform.

The time behaviour of the voltage drop with reference to the first and the second periods of time T1, T2, is shown in FIGS. 2a to 2c.

The current electrodes E2,E3 are connectable via fifth to eighth switches S5, S6, S7, S8 in a first or second polarity with the electrodes of a measuring capacitor C1.

The fifth, sixth, seventh and eighth switches S5 to S8 are also driven by the control device (not shown) which can be implemented as a microprocessor. The control is effected such that the voltage electrodes E2, E3 are connected with the measuring capacitor C1 during a third period of time T3 in the first polarity, and during a fourth period of time T4 in the second polarity. As can be seen from FIGS. 2d, 2e in view of FIGS. 2a, 2b, the third period of time T3 lies within the first period of time T1, and the fourth period of time T4 within the second period of time T2.

Ninth and tenth switches S9, S10 lie between the two electrodes of the measuring capacitor C1 and the inverting and non-inverting input of an operational amplifier OPV, respectively, whose output is connected to the inverted input thereof via a feedback capacitor C2.

The control device (not shown) connects during each fifth period of time which lies outside the third and the fourth periods of time T3,T4 the measuring capacitor C1 with the inputs of the operational amplifier OPV. According to the capacity relation of the feedback capacitor C2 and the measuring capacitor C1, the voltage at the measuring capacitor $V_{C1}$ is hereby amplified to a voltage produced at the output of the operational amplifier $V_{out}$.

In the shown embodiment the control device (not shown) closes at the end of each fifth period of time an eleventh switch S11, switched parallel to the feedback capacitor C2, so that the shown switched capacitor circuit S5 to S11, C1,C2, OPV works as amplifying circuit. It is, however, also possible to close the eleventh switch S11 after several periods of time T1, T2, so that the switched capacitor circuit operates as an integrating circuit in this case.

As can be taken from the course of the voltage drop over the voltage electrodes E2,E3 according to FIG. 2c, both, the first and the second periods have been selected long enough such that change-over effects fade out and voltage V1 takes on a substantially constant value. Only after fading out of the change-over processes the measuring capacitor is connected with the voltage electrodes during time period T3. On account thereof charge carriers flow over the voltage electrodes E2,3 onto the electrodes of the measuring capacitor C1. At the beginning of time period T3 this flow of current leads to a disturbance of the original field between current electrodes E1, E4 and to a momentary polarization. With increasing charging of the measuring capacitor C1 the measuring current at the voltage electrodes E2,E3 exponentially tends towards zero, so that the voltage electrodes E2,E3 become currentless when the time period T3 is sufficiently long. In a sufficiently long period of time T3, depending on the individual case, which can easily be determined in an experiment, however, the polarisation effects no longer have a negative influence on the obtainable measuring accuracy.

The conductivity measuring circuit according to the invention is suited for an integration of electrodes E1 to E4, the source of current circuit SQ and the amplifying electronic system including the switched capacitor circuit, on one single semiconductor substrate. On account of the monolithic integration on a semiconductor substrate, the conductivity measuring device according to the invention can be highly miniaturized, such that measurements are possible in small sample volumes or at other places which are hard to reach, as for example in invasive medical diagnostics.

The components of the circuit can be implemented in CMOS technology. In this case the manufacture of the electrodes can be compatible with the CMOS-process since merely the additional process step of applying a precious metal layer for the electrodes is required.

Despite the fact that the conductivity measuring circuit according to the invention is preferably suited for complete integration, also measuring circuits with separately arranged electrodes can be realized on the basis of the concept according to the invention.

I claim:

1. A conductivity measuring device for measuring the electric conductivity of liquids, said conductivity measuring device comprising:

a current source connectable to two current electrodes arranged for feeding a current with a rectangular waveform into the liquid, wherein said current does not contain any net DC component and a measuring circuit connected to two voltage electrodes for determining the voltage drop between the voltage electrodes which is dependent on the electric conductivity of the investigated liquid, wherein the measuring circuit is a switched capacitor circuit having a measuring capacitor, a feedback circuit with a feedback capacitor and feedback discharge switch arranged in a feedback branch thereof, and a switch mechanism connecting the measuring capacitor, in time-dependency with the current having the rectangular waveform, in one switching condition to the voltage electrodes and in another switching condition to the inputs of the feedback circuit.

2. A conductivity measuring device according to claim 1 wherein the current source comprises a DC current source which is connected via first, second, third and fourth switches with the current electrodes in first and second polarities.

3. A conductivity measuring device according to claim 2 further comprising a control device controlling the first, second, third and fourth switches in such a way that they connect the current source with the current electrodes alternately during a first period of time in the first polarity and during a second period of time in the second polarity.

4. A conductivity measuring device according to claim 3 wherein the switch mechanism has fifth, sixth, seventh and eight switches, the control device controls the fifth to eight switches in such a way that they connect the voltage electrodes with the measuring capacitor during a third period of time in a first polarity, and during a fourth period of time in a second polarity, and the third period of time lies within the first period of time and the fourth period of time lies within the second period of time.

5. A conductivity measuring device according to claim 3 wherein the first and the second periods of time are of equal length so that the time-average of the current having the rectangular waveform has a zero DC value.

6. A conductivity measuring device according to claim 1 wherein the switch arrangement has ninth and tenth switches, and the feedback circuit is connectable with the measuring capacitor via the ninth and tenth switches.

7. A conductivity measuring device according to claim 6 wherein the control device controls the ninth and tenth switches in such a way that they connect the amplifying circuit during a fifth period of time, lying outside the third and the fourth period of time, with the measuring capacitor.

8. A conductivity measuring device according to claim 1 further comprising a control device that controls the feedback discharge switch to discharge the feedback capacitor after each fifth period of time.

9. A conductivity measuring device according to claim 1 further comprising a control device that controls the feedback discharge switch to discharge the feedback capacitor after a plurality of periods.

* * * * *